United States Patent [19]

Ruegsegger

[11] Patent Number: 4,786,251

[45] Date of Patent: Nov. 22, 1988

[54] DENTAL HANDPIECE AND HIGH SPEED TURBINE ASSEMBLY

[75] Inventor: Neil C. Ruegsegger, Torrance, Calif.

[73] Assignee: James E. Shenberg, Los Angeles, Calif.

[21] Appl. No.: 917,662

[22] Filed: Oct. 10, 1986

[51] Int. Cl.[4] ............................................. A61C 1/05
[52] U.S. Cl. ................................. 433/132; 415/106; 415/503
[58] Field of Search ..................... 433/132, 91, 92, 82, 433/99, 84, 126; 415/106, 100, 104, 503, 202

[56] References Cited

U.S. PATENT DOCUMENTS

| 1,151,965 | 8/1915 | Peterson | 415/106 |
| 2,340,787 | 2/1944 | Zenner et al. | 415/100 |
| 2,455,460 | 12/1948 | Zenner | 415/104 |
| 3,077,333 | 2/1963 | Gotwald, Jr. et al. | 415/202 |
| 3,092,908 | 6/1963 | Flatland | 433/132 |
| 3,101,541 | 8/1963 | Hoffmeister | 433/82 |
| 3,132,426 | 5/1964 | White | 433/132 |
| 3,189,999 | 6/1965 | Reiter | 433/132 |
| 3,248,792 | 5/1966 | Staunt | 433/99 |
| 3,364,576 | 1/1968 | Kern, Jr. | 433/82 |
| 3,477,636 | 11/1969 | Gessner | 415/100 |
| 4,249,896 | 2/1981 | Kerfoot, Jr. | 433/126 |
| 4,253,831 | 3/1981 | Eaton, II | 433/91 |

*Primary Examiner*—John J. Wilson
*Attorney, Agent, or Firm*—Keith D. Beecher

[57] ABSTRACT

A dental handpiece which includes a high speed compressed-air driven turbine at the distal end thereof which serves to drive a dental drill, or other element. The handpiece includes an internal conduit for supplying compressed air to the turbine and an exit port for exhausting the compressed air. In accordance with the concepts of the invention, the exit port is coupled to a vacuum pump, or other vacuum source, to enhance the turbine efficiency and to provide for increased power output with significant noise suppression, and also to facilitate the use of in-line oil mist lubrication.

5 Claims, 2 Drawing Sheets

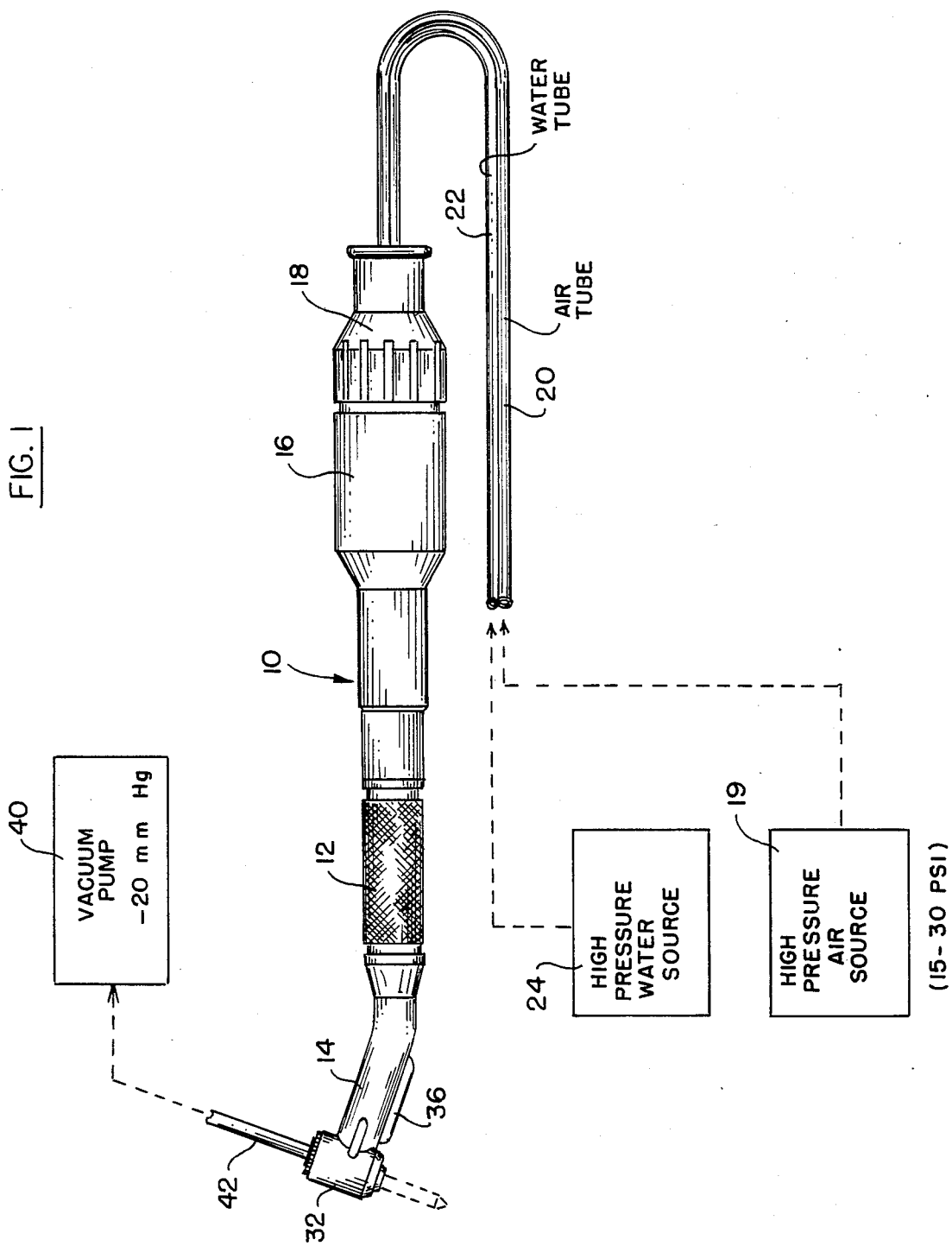

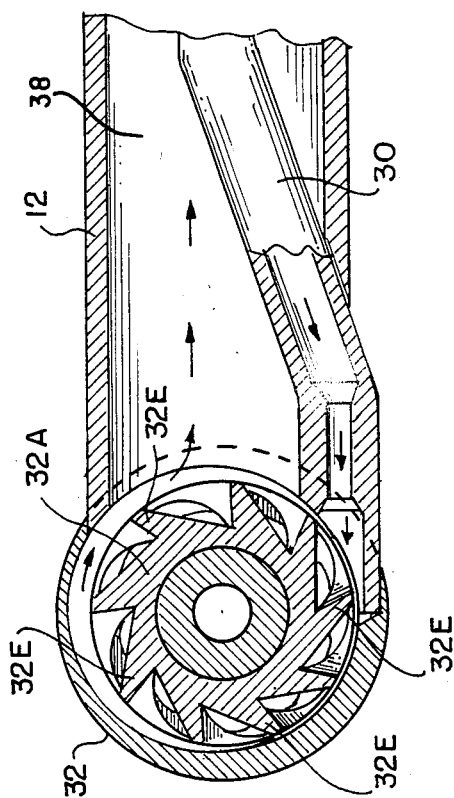
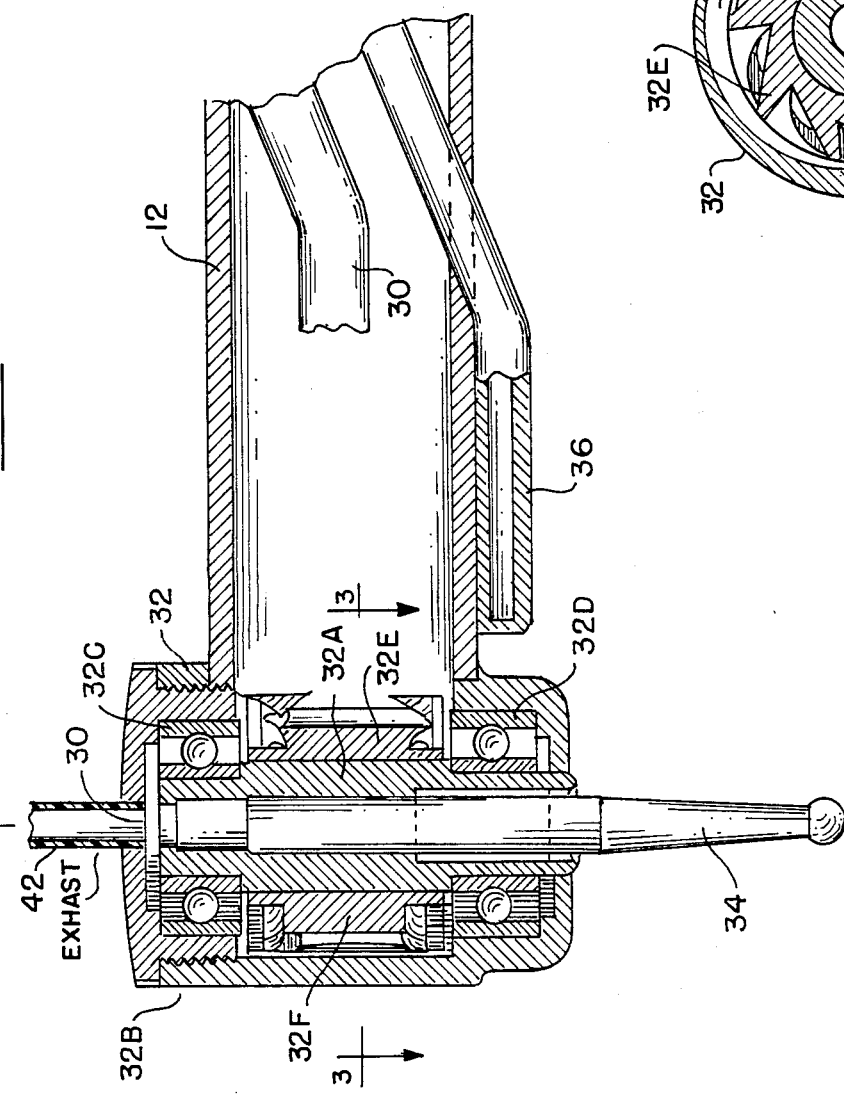

DENTAL HANDPIECE AND HIGH SPEED TURBINE ASSEMBLY

BACKGROUND OF THE INVENTION

The dental handpiece of the invention may be of the type which includes a tubular main body with connecting means at one end of the body for hoses from a compressed air and pressurized water supply; and having conduits extending longitudinally through the body which are coupled to the hoses to supply a stream of water adjacent to the other end of the body, and also to supply compressed air to a high speed turbine mounted at the other end of the body.

The compressed air is directed into the turbine to impinge on the blades of a rotor contained within the turbine housing. The turbine rotor is mounted on bearings at each end of the housing, the bearings being lubricated by oil mist carried by the incoming compressed air.

An exhaust port is provided at one end of the housing, the exhaust port being coupled to an appropriate vacuum source through a hose. This expedient serves to increase the power output of the turbine which, in turn, permits the turbine to be operated at lower speeds than the prior art handpieces for a desired torque output with resulting decrease in the noise level of the instrument. This feature also permits smaller hoses to be used for supplying the compressed air to the turbine, as compared with the hoses used in the prior art handpieces to achieve an equivalent output torque.

Accordingly, the primary objective of the present invention is to provide an improved dental handpiece apparatus of increased efficiency as compared with the prior art apparatus, and which is capable of producing a desired torque at lower speeds and lower noise level than is possible with the prior art apparatus.

BRIEF DESCRIPTION OF THE DRAWINGS

FIG. 1 is a side elevational view of a dental handpiece with air and water hoses attached thereto, and with the exhaust port thereof coupled through an additional hose to an appropriate vacuum source;

FIG. 2 is a sectional view on an enlarged scale, as compared with FIG. 1, of the high speed turbine included in the handpiece of FIG. 1; and FIG. 3 is a cross-sectional view of the turbine taken essentially along the line 3—3 of FIG. 2.

DETAILED DESCRIPTION OF THE ILLUSTRATED EMBODIMENT

The dental handpiece, designated generally as 10 in FIG. 1, is a contra-angle type having a tubular main body 12 which receives a contra-angle tubular body 14 in a telescoping slip-fit, with bodies 12 and 14 being secured to one another by soldering or welding. The other end of body 12 receives an enlarged tubular housing 16 in a telescoping slip-fit, with body 12 being attached to housing 16 by welding or soldering. A coupling section 18 is mounted on one end of housing 16.

A high pressure air hose 20 extends into section 18 from a high pressure air pump, or other source 19, to supply compressed air to the handpiece in a range, for example, of 15–30 psi. Likewise, a high pressure water hose 22 extends into section 18 from a high pressure water pump, or other source, 24. Air hose 20 is connected to a conduit 30 (FIGS. 2 and 3) in section 18 which extends along the tubular body 12 to supply compressed air to a turbine 32 mounted at the other end of the tubular body 12.

Turbine 32 includes a rotor 32A which is rotatably mounted in a turbine housing 32B on bearings 32C and 32D. A dental burr, drill, or other element, 34 is removably received in rotor 32A in coaxial relationship. Rotor 32A includes a series of vanes 32E, and conduit 30 directs compressed air against the rotor vanes to cause the rotor to drive the dental element 34. The water hose 22 is connected to a conduit 36 (FIG. 2) in section 18. Conduit 36 extends through body 12, and it provides a cooling water spray adjacent to dental element 34.

Oil mist carried by the compressed air is supplied to bearings 32C and 32D for lubrication purposes, as the compressed air passes through the turbine and out an exit port 38. The exit port 38 is coupled to a vacuum pump, or other vacuum source 40, by means of a hose 42. Vacuum source 40, for example, provides a vacuum of −20 millimeters of mercury.

The invention provides, therefore, an improved dental handpiece which includes a turbine driven by compressed air, and whose exhaust is coupled to a vacuum source for increased efficiency, and for other desirable effects and features described above.

It will be appreciated that while a particular embodiment of the invention has been shown and described, modifications may be made. It is intended in the claims to cover all modifications which come within the spirit and scope of the invention.

I claim:

1. A dental handpiece comprising: an elongated tubular body; a turbine housing mounted at one end of said tubular body and having an entrance port and an exit port; a rotor rotatably mounted in said housing having a plurality of vanes; means for mounting a dental element on said rotor in coaxial relationship therewith; a source of compressed air; conduit means within said housing; means coupling said conduit means to said source for causing said conduit means to supply compressed air through said entrance port to said vanes to cause said rotor to rotate and impart a driving torque to said dental element; a vacuum pressure source; and means coupling said exit port to said vacuum pressure source for establishing a vacuum pressure at said exit port so as to increase the torque imparted by said compressed air to said dental element.

2. The dental handpiece defined in claim 1, and which includes a hose extending to the other end of said tubular body to couple said conduit means to said source of said compressed air.

3. The dental handpiece defined in claim 1, and which includes a hose coupling said exit port to said vacuum pressure source.

4. The dental handpiece defined in claim 1, in which said compressed air is pressurized in the range of substantially 15–30 psi.

5. The dental handpiece defined in claim 1, in which the vacuum pressure of said vacuum pressure source is of the order of −20 millimeters of mercury.

* * * * *